(12) United States Patent
Krummen (10) Patent No.: US 11,338,131 B1
(45) Date of Patent: May 24, 2022

(54) GUIDING IMPLANTATION OF AN ENERGY DELIVERY COMPONENT IN A BODY

(71) Applicant: Vektor Medical, Inc., Carlsbad, CA (US)

(72) Inventor: Robert Joseph Krummen, Bellevue, WA (US)

(73) Assignee: Vektor Medical, Inc., Carlsbad, CA (US)

( * ) Notice: Subject to any disclaimer, the term of this patent is extended or adjusted under 35 U.S.C. 154(b) by 0 days.

(21) Appl. No.: 17/308,400

(22) Filed: May 5, 2021

(51) Int. Cl.
| | |
|---|---|
| *A61N 1/05* | (2006.01) |
| *A61N 1/368* | (2006.01) |
| *G16H 10/60* | (2018.01) |
| *G06N 20/10* | (2019.01) |
| *G16H 40/63* | (2018.01) |

(Continued)

(52) U.S. Cl.
CPC .......... *A61N 1/0587* (2013.01); *A61N 1/3684* (2013.01); *G06N 20/10* (2019.01); *G16H 10/60* (2018.01); *G16H 20/40* (2018.01); *G16H 40/63* (2018.01); *G16H 50/70* (2018.01)

(58) Field of Classification Search
CPC ... A61B 34/10; A61B 34/20; A61B 2034/101; A61B 2034/107; A61B 2034/2046; A61B 5/318
See application file for complete search history.

(56) References Cited

U.S. PATENT DOCUMENTS

| | | | |
|---|---|---|---|
| 4,352,163 A | 9/1982 | Schultz et al. | |
| 5,458,116 A | 10/1995 | Egler | |
| 5,596,634 A | 1/1997 | Fernandez et al. | |

(Continued)

FOREIGN PATENT DOCUMENTS

| | | |
|---|---|---|
| CN | 105263405 A | 1/2016 |
| CN | 106725428 | 5/2017 |

(Continued)

OTHER PUBLICATIONS

Andreu et al., "Integration of 3D Electroanatomic Maps and Magnetic Resonance Scar Characterization Into the Navigation System to Guide Ventricular Tachycardia Ablation", Circ Arrhythm Electrophysiol, Oct. 2011, 4(5), pp. 674-683.

(Continued)

*Primary Examiner* — John R Downey
(74) *Attorney, Agent, or Firm* — Perkins Coie LLP (57) ABSTRACT

A system for guiding implantation of an energy delivery component of a cardiac pacing device at a fixation location within a heart of a patient is provided. During a procedure to implant an energy pulse delivery component, the system receives a patient cardiogram collected during pacing of the energy pulse delivery component while the energy pulse delivery component is positioned at a current location within the heart. The system then determines based on the patient cardiogram the current location of the energy pulse delivery component. The system then outputs an indication of the current location to guide affixing of the energy pulse delivery component at the intended fixation location. This process is repeated until the energy pulse delivery component is at the fixation location. The system also evaluates the effectiveness of pacing at intermediate location to optimize the final location based upon simulated electro-mechanics of the system in near-real time.

6 Claims, 6 Drawing Sheets

(51) Int. Cl.
*G16H 50/70* (2018.01)
*G16H 20/40* (2018.01)

(56) References Cited

U.S. PATENT DOCUMENTS

| | | | |
|---|---|---|---|
| 5,803,084 A | 9/1998 | Olson | |
| 5,891,132 A | 4/1999 | Hohla | |
| 6,269,336 B1 | 7/2001 | Ladd et al. | |
| 6,292,783 B1 | 9/2001 | Rohler et al. | |
| 6,324,513 B1 | 11/2001 | Nagai et al. | |
| 6,567,805 B1 | 5/2003 | Johnson et al. | |
| 6,895,084 B1 | 5/2005 | Saylor et al. | |
| 6,931,273 B2 | 8/2005 | Groenewegen et al. | |
| 7,286,866 B2 | 10/2007 | Okerlund et al. | |
| 8,224,640 B2 | 7/2012 | Sharma et al. | |
| 8,521,266 B2 | 8/2013 | Narayan | |
| 8,838,203 B2 | 9/2014 | Van Dam et al. | |
| 8,849,389 B2 | 9/2014 | Anderson et al. | |
| 9,014,795 B1 | 4/2015 | Yang | |
| 9,129,053 B2 | 9/2015 | Mansi et al. | |
| 9,277,970 B2 | 3/2016 | Mansi et al. | |
| 9,320,126 B2 | 4/2016 | Valcore, Jr. | |
| 9,706,935 B2 | 7/2017 | Spector | |
| 9,842,725 B2 | 12/2017 | Valcore, Jr. | |
| 10,039,454 B2 | 8/2018 | Sapp, Jr. et al. | |
| 10,311,978 B2 | 6/2019 | Mansi et al. | |
| 10,319,144 B2 | 6/2019 | Krummen et al. | |
| 10,342,620 B2 | 7/2019 | Kiraly et al. | |
| 10,363,100 B2 | 7/2019 | Trayanova et al. | |
| 10,556,113 B2 | 2/2020 | Villongco | |
| 10,617,314 B1 | 4/2020 | Villongco | |
| 10,713,790 B2 * | 7/2020 | Adler | G06T 7/74 |
| 10,860,754 B2 | 12/2020 | Villongco | |
| 2001/0049688 A1 | 12/2001 | Fratkina et al. | |
| 2002/0010679 A1 | 1/2002 | Felsher | |
| 2002/0154153 A1 | 10/2002 | Messinger | |
| 2002/0188599 A1 | 12/2002 | McGreevy | |
| 2003/0182124 A1 | 9/2003 | Khan | |
| 2004/0083092 A1 | 4/2004 | Valles | |
| 2004/0176697 A1 | 9/2004 | Kappenberger | |
| 2007/0032733 A1 | 2/2007 | Burton | |
| 2008/0140143 A1 | 6/2008 | Ettori | |
| 2008/0177192 A1 | 7/2008 | Chen | |
| 2008/0234576 A1 * | 9/2008 | Gavit-Houdant | A61B 34/20 600/434 |
| 2009/0099468 A1 | 4/2009 | Thiagalingam | |
| 2009/0275850 A1 | 11/2009 | Mehendale | |
| 2011/0028848 A1 | 2/2011 | Shaquer | |
| 2011/0118590 A1 | 5/2011 | Zhang | |
| 2011/0251505 A1 | 10/2011 | Narayan | |
| 2011/0307231 A1 | 12/2011 | Kirchner | |
| 2012/0173576 A1 | 7/2012 | Gillam et al. | |
| 2013/0006131 A1 | 1/2013 | Narayan | |
| 2013/0096394 A1 | 4/2013 | Gupta | |
| 2013/0131529 A1 | 5/2013 | Jia | |
| 2013/0131629 A1 | 5/2013 | Jia | |
| 2013/0150742 A1 | 6/2013 | Briggs | |
| 2013/0197881 A1 | 8/2013 | Mansi et al. | |
| 2013/0268284 A1 | 10/2013 | Heck | |
| 2013/0304445 A1 | 11/2013 | Iwamura et al. | |
| 2014/0005562 A1 | 1/2014 | Bunch | |
| 2014/0088943 A1 | 3/2014 | Trayanova et al. | |
| 2014/0107511 A1 | 4/2014 | Banet | |
| 2014/0122048 A1 | 5/2014 | Vadakkumpadan et al. | |
| 2014/0200575 A1 | 7/2014 | Spector | |
| 2014/0276152 A1 | 9/2014 | Narayan | |
| 2015/0005652 A1 | 1/2015 | Banet et al. | |
| 2015/0057522 A1 | 2/2015 | Nguyen | |
| 2015/0216432 A1 | 8/2015 | Yang | |
| 2015/0216434 A1 | 8/2015 | Ghosh | |
| 2015/0216438 A1 | 8/2015 | Bokan et al. | |
| 2015/0294082 A1 | 10/2015 | Passerini et al. | |
| 2016/0008635 A1 | 1/2016 | Burdette | |
| 2016/0038743 A1 * | 2/2016 | Foster | A61N 1/37512 607/116 |
| 2016/0113725 A1 | 4/2016 | Trayanova et al. | |
| 2016/0135702 A1 | 5/2016 | Perez | |
| 2016/0135706 A1 | 5/2016 | Sullivan | |
| 2016/0331337 A1 | 11/2016 | Ben-Haim | |
| 2017/0027649 A1 | 2/2017 | Kiraly | |
| 2017/0061617 A1 | 3/2017 | Cochet | |
| 2017/0065195 A1 | 3/2017 | Nguyen | |
| 2017/0068796 A1 | 3/2017 | Passerini et al. | |
| 2017/0079542 A1 | 3/2017 | Spector | |
| 2017/0150928 A1 | 6/2017 | del Alamo de Pedro | |
| 2017/0156612 A1 | 6/2017 | Relan | |
| 2017/0161439 A1 | 6/2017 | Raduchel et al. | |
| 2017/0178403 A1 * | 6/2017 | Krummen | G06T 17/20 |
| 2017/0185740 A1 | 6/2017 | Seegerer | |
| 2017/0202421 A1 | 7/2017 | Hwang et al. | |
| 2017/0202521 A1 | 7/2017 | Urman et al. | |
| 2017/0209698 A1 | 7/2017 | Villongco | |
| 2017/0231505 A1 | 8/2017 | Mahajan | |
| 2017/0273588 A1 | 9/2017 | He | |
| 2017/0027465 A1 | 11/2017 | Blauer | |
| 2017/0319089 A1 | 11/2017 | Lou | |
| 2017/0319278 A1 | 11/2017 | Trayanova | |
| 2017/0330075 A1 | 11/2017 | Tuysuzoglu | |
| 2017/0367603 A1 | 12/2017 | Spector | |
| 2018/0020916 A1 | 1/2018 | Ruppersberg | |
| 2018/0260706 A1 * | 9/2018 | Galloway | A61B 5/7221 |
| 2018/0279896 A1 | 10/2018 | Ruppersberg | |
| 2018/0318606 A1 | 11/2018 | Robinson | |
| 2019/0038363 A1 * | 2/2019 | Adler | A61B 34/25 |
| 2019/0060006 A1 | 2/2019 | Van Dam | |
| 2019/0069795 A1 | 3/2019 | Kiranya | |
| 2019/0104951 A1 | 4/2019 | Valys | |
| 2019/0104958 A1 | 4/2019 | Rappel | |
| 2019/0125186 A1 | 5/2019 | Ruppersberg | |
| 2019/0223946 A1 | 7/2019 | Coates | |
| 2019/0304183 A1 * | 10/2019 | Krummen | A61B 5/361 |
| 2019/0328254 A1 * | 10/2019 | Villongco | A61B 5/7435 |
| 2019/0328257 A1 * | 10/2019 | Villongco | A61B 5/319 |
| 2019/0328457 A1 * | 10/2019 | Villongco | A61B 5/7203 |
| 2019/0328458 A1 | 10/2019 | Shmayahu | |
| 2019/0332729 A1 * | 10/2019 | Villongco | G16H 30/40 |
| 2020/0324118 A1 * | 10/2020 | Garner | A61N 1/36592 |
| 2021/0015390 A1 * | 1/2021 | Zhou | A61N 1/08 |
| 2021/0205025 A1 * | 7/2021 | Erkamp | A61B 8/4254 |

FOREIGN PATENT DOCUMENTS

| | | |
|---|---|---|
| JP | H08289877 A | 11/1996 |
| JP | 2017-140381 A | 8/2017 |
| WO | 2015153832 A1 | 10/2015 |
| WO | 2018190715 A1 | 10/2018 |
| WO | 2019118640 A1 | 6/2019 |

OTHER PUBLICATIONS

Acharya et al., A deep convolutional neural network model to classify heartbeats, Computers in Biology and Medicine (Oct. 1, 2017) vol. 89, pp. 389-396.

Acharya et al., Deep convolutional neural network for the automated detection and diagnosis of seizure using EEG signals, Computers in Biology and Medicine (Sep. 1, 2018, Epub Sep. 27, 2017) 100:270-278.

Carrault, Guy, et al. "A model-based approach for learning to identify cardia arrhythias," Joint European Conference on Artificial Intellegence in Medicine and Medicine Decision Making. Springer, Berline Heidelberg, 1999.

Carrualt, Guy, et al. "Temporal abstraction and inductive logic programming for arrhythima recognition from electrocardiograms." Artificial intelligence in medicine 28.3 (2003): 231-263.

Cobb, Leonard A., et al. "Changing incidence of out-of-hospital ventricular fibrillation, 1980-2000." Jama 288.23 (2002): 3008-3013.

Cuculich, Phillip S. et al., "Noninvasive Cardiac Radiation for Ablation of Ventricular Tachycardia" New England Journal of Medicine, 377; 24, pp. 2325-2336, Dec. 14, 2017.

(56) References Cited

OTHER PUBLICATIONS

Dandu Ravi Varma, "Managing DICOM images: Tips and tricks for the radiologist", Indian J Radiol Imaging., Jan.-Mar. 20212; 22(1), pp. 4-13.
Extended European Search Report issued in European Patent Application No. 19215701.4 and dated Apr. 17, 2020, 9 pages.
Extended European Search Report issued in European Patent Application No. 19792821.1 and dated Mar. 15, 2021. 10 pages.
Frank, Ernest, "An Accurate, Clinically Practical System for Spatial Vectorcardiography," American Heart Association, Inc., downloaded from http://circ.ahajournals.org/ at Cons California Dig Lib on Mar. 12, 2014.
Gonzales, Matthew J., et al. "Structural contributions to fibrillatory rotors in a patient-derived computational model of the atria." EP Europace 16.suppl 4 (2014): iv3-iv10.
Graham, Adam J. et al., "Evaluation of ECG Imaging to Map Haemodynamically Stable and Unstable Ventricular Arrhythmias" downloaded from http://ahajournals.org on Jan. 22, 2020.
Hren, Rok, et al. "Value of simulated body surface potential maps as templates in localizing sites of ectopic activation for radiofrequency ablation" Physiol. Meas. 18 (1997) 373-400. Mar. 7, 1997.
International Search Report and Written Opinion issued for PCT/US16/68449 dated Mar. 29, 2017.
International Search Report and Written Opinion issued for PCT/US2019/029181 dated Sep. 16, 2019.
International Search Report and Written Opinion issued for PCT/US2019/029184 dated Sep. 24, 2019.
International Search Report and Written Opinion issued for PCT/US2019/058217 dated Feb. 7, 2020, 9 pages.
International Search Report and Written Opinion issued for PCT/US2019/069136 dated May 11, 2020, 13 pages.
International Search Report and Written Opinion issued in PCT/US2020/036754 dated Oct. 15, 2020, 13 pages.
Jacquemet, V., "Lessons from Computer Simulation of Ablation of Atrial Fibrillation", J Physiol. 594(9): 2417-2430, May 1, 2016.
Kiranyaz et al., Real-time patient-specific EDG classification by 1-D convolutional neural networks, IEEE Transactions on Biomedical Engineering (Mar. 2016) 63:664-675.
Kors, J.A., et al., "Recontruction of the Frank vectorcardiogram from standard electrocardiographic leads: diagnostic comparison of different methods," European Heart Journal, vol. 11, Issue 12, Dec. 1, 1990, pp. 1083-1092.
Krishnamurthy, Adarsh, et al. "CRT Response is Greater in Patients With Larger Fraction of the Myocardium Performing Negative Regional Work." Circulation 128.Suppl 22 (2013): A11135-A11135, Abstract only.
Krishnamurthy, Adarsh, et al. "Patient-specific models of cardiac biomechanics." Journal of computational physics 244 (2013): 4-21.
Krummen, David E., et al. "Rotor stability separates sustained ventricular fibrillation from selfterminating episodes in humans." Journal of the American College of Cardiology 63.24 (2014): 2712-2721.
Lyon, et al. J.R. Soc Interface vol. 15:1-18. (2017).
Nash, Martyn P., et al. "Evidence for multiple mechanisms in human ventricular fibrillation." Circulation 114.6 (2006): 536-542.
Potse, Mark et al., "Continues Localization of Cardian Activation Sites Using a Database of Multichannel ECG Recordings" IEEE Transactions of Biomedical Engineering, vol. 47, No. 5, May 2000, pp. 682-689.
Rahhal et al., Convolutional neural networks for electrocardiogram classification, Journal of Medical and Biological Engineering (Mar. 30, 2018) 38: 1014-1025.
Sapp, John L. et al., "Real-Time Localization of Ventricular Tachycardia Origin From the 12-Lead Electrocardiogram" JACC: Clinical Electrophysiology by the American College of Cardiology Foundation, vol. 3, 2017, pp. 687-699.
Si, Hang, "TetGen, a Delaunay-Based Quality Tetrahedral Mesh Generator," ACM Transactions on Mathematical Software, vol. 41, No. 2, Article 11, Jan. 2015, 36 pages.
Siregar, P. "An Interactive Qualitative Model in Cardiology" Computers and Biomedical Research 28, pp. 443-478, May 16, 1994.
Taggart, Peter, et al. "Developing a novel comprehensive framework for the investigation of cellular and whole heart electrophysiology in the in situ human heart: Historical perspectives, current progress and future prospects." Progress in biophysics and molecular biology 115 (2014): 252-260.
Tajbakhsh, Nima et al., "Convolutional Neural Networks for Medical Image Analysis: Full Training or Fine Tuning?" IEEE Transactions on Medical Imaging (2016) vol. 35, e-pp. 1-17).
Ten Tusscher et al. "A model for human ventricular tissue." American Journal of PhysioloQy-Heart and Circulatory Physiology 286 (2004): H1573-H1589.
Thakor and Tong (Annual Reviews in Biomedicine and Engineering (2004) vol. 6, 453-495).
Tobon, Catalina, et al. "Dominant frequency and organization index maps in a realistic three-dimensional computational model of atrial fibrillation." Europace; 14, suppl_5 (2012): v25-v32.
Tomašić, Ivan et al., "Electrocardiographic Systems With Reduced Numbers of Leads—Synthesis of the 12-Lead ECG," IEEE Reviews in Biomedical Engineering, vol. 7, 2014, pp. 126-142.
Vadakkumpadan, Fijoy, et al. "Image-based estimation of ventricular fiber orientations for personalized modeling of cardiac electrophysiology." IEEE (2012): 1051-1060.
Villongco, Christopher T., et al. "Patient-specific modeling of ventricular activation pattern using surface ECG-derived vectorcardiogram in bundle branch block." Progress in biophysics and molecular biology 115.2 (2014): 305-313.
Vozda, M. et al., "Methods for derivation of orthogonal leads from 12-lead electrocardiogram: A review," Elsevier, Biomedical Signal Processing and Control 19 (2015), 23-34.
Xiong et al. "Robust ECG Signal Classification for Detection of Atrial Fibrillation Using a Novel Neural Network" Computing and Cardiology vol. 44: pp. 1-4. (2017).
Zhou, Shijie et al. "Localization of ventricular activation origin using patient-specific geometry: Preliminary results" J. Carciovasc Electrophysiol, 2018; 29: pp. 979-986.
Zhou, Shijie et al. "Rapid 12-lead automated localization method: Comparison to electrocardiographic imaging (ECGI) in patient-specific geometry", Journal of Electrocardiology, vol. 51, 2018, pp. S92-S97.
Light, D., E., et al. "Two Dimensional Arrays for Real Time Volumetric and Intracardiac Imaging with Simultaneous Electrocardiagram", 1196-2000 IEEE Ultrasonics Symposium, retrieved on Sep. 24, 2021.
Zhang, C., et al. "Patient-Specific ECG Classification Based on Recurrent Neural Networks and Clustering Technique," Proceedings of the IASTED International Conference in Biomedical Engineering (Bio Med 2017); Feb. 20-21, 2017 in Innsbruck, Austria, 5 pages.

* cited by examiner

GUIDING IMPLANTATION OF AN ENERGY DELIVERY COMPONENT IN A BODY

BACKGROUND

Many fast heart disorders can cause symptoms, morbidity (e.g., syncope or stroke), and mortality. Common heart disorders caused by rapid arrhythmias include inappropriate sinus tachycardia ("IST"), ectopic atrial rhythm, accelerated junctional rhythm, ventricular escape rhythm, atrial fibrillation ("AF"), ventricular fibrillation ("VF"), focal atrial tachycardia ("focal AT"), atrial microreentry, ventricular tachycardia ("VT"), atrial flutter ("AFL"), premature ventricular complexes ("PVCs"), premature atrial complexes ("PACs"), atrioventricular nodal reentrant tachycardia ("AVNRT"), atrioventricular reentrant tachycardia ("AVRT"), permanent junctional reciprocating tachycardia ("PJRT"), and junctional tachycardia ("JT"). The sources of rapid arrhythmias may include electrical rotors (e.g., ventricular fibrillation), recurring electrical focal sources (e.g., atrial tachycardia), anatomically based reentry (e.g., ventricular tachycardia), and so on. These sources are important drivers of sustained or clinically significant episodes. Arrhythmias can be treated with ablation using different technologies, including radiofrequency energy ablation, cryoablation, ultrasound ablation, laser ablation, external radiation sources, directed gene therapy, and so on by targeting the source of the heart disorder. Since the sources of heart disorders and the locations of the source vary from patient to patient, even for common heart disorders, targeted therapies require the source of the arrhythmia, or the atrioventricular node to achieve complete heart block and slow ventricular rate response, to be identified.

Slow heart rhythms include sinus bradycardia, sinus node exit block, first degree atrioventricular block, second degree atrioventricular block type 1, second degree atrioventricular block type 2, third degree atrioventricular block (complete heart block), left bundle branch block, right bundle branch block, left anterior fascicular block, left posterior fascicular block, and bi-fascicular block.

Depending on the type and severity of an arrhythmia, an implantable pacemaker or an implantable cardioverter-defibrillator may be an option for treating the arrhythmia. A pacemaker/ICD ("pacemaker") typically includes an electrode, a lead (except in the case of leadless pacemakers), and a pulse generator. To implant the pacemaker, the lead and electrode are inserted into a vein and then moved into the heart so that the electrode is positioned at and affixed to a target fixation location. The pulse generator may be implanted under the skin near the heart (or physically connected to the electrode in the case of a leadless pacemaker).

A pacemaker/ICD may also be used to treat heart failure caused by problems with the dyssynchrony between the upper and lower and/or the left and right heart chambers. One such treatment is cardiac resynchronization therapy (CRT). CRT involves placement of multiple electrodes of a CRT device (i.e., a type of pacemaker) in the heart to control the timing of and activation locations of the heart beats. A CRT device typically employs three or more electrodes connected via leads to a pulse generator that controls, for example, biventricular pacing of the heart.

To determine the locations of an electrode as it is moved within the heart to the target fixation location, X-rays are taken of the heart at various intervals. An electrophysiologist uses the X-rays to determine how next to move the electrode. When the electrode reaches the target fixation location, the electrophysiologist places or affixes the electrode to the endocardium at its current location.

The use of X-rays (or other imaging devices) to guide implantation can be both expensive and cumbersome. In addition, the intended fixation location may not be the most feasible or effective fixation location in part because of limitations in patients anatomy such as the presence of block in the coronary sinus branches, the presence of scar or other myocardial disease in the atria or ventricles which limit the ability to pace the heart, the presence of thrombus at the intended fixation location, etc. For example, a more effective fixation location may be 1.0 cm away from the target fixation location. So, while affixing the electrode to the target fixation location may be somewhat effective, it may not be as effective as another fixation location.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

A method and system for guiding implantation of an implantable electromagnetic device in a body is provided. An implantable electromagnetic device may include an energy delivery component (e.g., electrode) and an electrical generator component (e.g., battery and pulse controller). An implantable electromagnetic device (IEMD) may also include a lead connecting the energy pulse generator component (EPGC) to the energy pulse delivery component (EPDC). The IEMD may also be leadless in the sense that the EPGC and the EPDC are housed within a capsule that is implanted within the body. An IEMD (e.g., cardiac device) may be a standard pacemaker, biventricular pacemaker, implantable cardioverter defibrillator, cardiac loop recorder, leadless pacemaker, cardiac resynchronization therapy device, and so on. In the following, an implantation guidance (IG) system is described primarily in the context of a heart but may be used with other electromagnetic sources such as organs (e.g., brain or lungs). More generally, an organ may be within the circulatory system, the nervous system, the digestive system, the respiratory system, and so on. The EPDC may be affixed to the organ at a fixation location that is within the organ or that is outside the organ. The EPGC may be positioned within or at a position near the organ. When the EPDC delivers energy to an organ, an electrogram (e.g., electroencephalogram) indicating response of the organ to the energy may be collected and used to determine the location of the EPDC.

In some embodiments, an IG system provides guidance for positioning the EPDC at a fixation location within the heart for affixing the EPDC within the heart. During implantation, the EPDC is guided along a path from the entry point within the heart (e.g., internally via a vein, or externally via the pericardial space, or externally via the coronary sinus and its tributaries) to the fixation location. As the EPDC is moved through the heart, the EPDC is placed in contact with endocardium at various locations and activated to provide electromagnetic pulses to the heart referred to as pacing. Patient cardiograms (e.g., electrocardiograms or vectorcardiograms) are collected during the pacing. The IG system compares the patient cardiograms to library cardiograms in a cardiogram library of library cardiograms. Each library cardiogram is associated with an activation location within a heart. The library cardiograms may be generated as described in U.S. Pat. No. 10,860,745, entitled "Calibration of Simulated Cardiograms" and issued on Dec. 8, 2020, which is hereby incorporated by reference. The activation location associated with a cardiogram is the location at which a cardiac cycle originates (e.g., via a simulated activation, a clinical initiated activation, or a patient activation) resulting in that cardiogram. The IG system identifies a library cardiogram that matches the patient cardiogram and outputs the activation location associated with the matching library cardiogram. The IG system outputs an indication of that activation location to represent the current location of the EPDC. The process of placing the EPDC in contact with the endocardium, pacing the EPDC, collecting cardiograms, and identifying the current location of the EPDC can be repeatedly performed until the EPDC is located at the fixation location. In this way, the EPDC can be accurately guided to the fixation location without the need and capital equipment expense of using fluoroscopy (X-ray imaging) during an implantation procedure.

In some embodiments, the IG system may be provided with a target path from entry into the heart to the fixation location. A target path may be through an atrium and then into a ventricle. Another target path may be into an atrium, through the ostium of the coronary sinus, into the body of the coronary sinus, and out a branch of the coronary sinus. A target path may also include the portion of the vein from the entry point into the vein to the entry point into the heart. The IG system may display a graphic that shows a heart with an indication of the path superimposed on the heart. As the EPDC travels to the fixation location, the IG system can superimpose on the graphic indications of the activation locations so that the electrophysiologist can view the activation location (and previous activation locations) to determine the current position of the EPDC and guide movement of the EPDC accordingly. The IG system may also suggest a next activation location to continue along the path, to move back to the path after a deviation, or to move along an alternative path (e.g., an updated path). The IG system may employ a deviation criterion to determine whether a deviation is considered significant enough to update the target path. For example, the deviation criterion may be a threshold distance from the target path. The threshold distance may vary based on the chamber in which the EPDC is currently located, distance to the endocardium, distance to the target fixation location, and so on. The graphic of a heart may be derived from measurements collected from the patient or from the geometry of a heart associated with a library cardiogram. For example, a patient cardiogram may be collected during normal sinus rhythm and compared to library cardiogram to identify a matching library cardiogram. The IG system may generate the graphic based on the geometry associated with the matching library cardiogram.

In some embodiments, the IG system may interface with an ultrasound device to collect echocardiograms as the EPDC travels from the entry point into the vein to the entry point into the heart. Since the vein is not part of the heart, the delivery of a pulse to the endothelium of the vein will not cause activation of the heart. The use of the ultrasound device to track the EPDC within the vein and along with the use of endocardium pacing allows for tracking of the EPDC from the entry point into the vein to the fixation location.

In some embodiments, once the EPDC is near a target fixation location, the EPDC may be activated at various activation locations near the target fixation location to evaluate the effectiveness of the activation locations as the actual fixation location. The IG system collects a patient cardiogram for each activation location near the target fixation location. The IG system then compares the patient cardiogram to a target cardiogram (e.g., indicating a desired sinus rhythm) to identify an activation location resulting in a patient cardiogram that matches a target cardiogram (e.g., cosine similarity or Pearson similarity based on vectorcardiograms). The EPDC may then be implanted at the identified activation location—that is the actual fixation location.

In some embodiment, the IG system may be employed to guide a catheter during an ablation procedure. The catheter may have an EPDC attached near the end of the catheter. As the catheter moves toward a target ablation location, the EPDC may be activated, when in contact with the endocardium, to identify the activation location as described above. When the identified activation location is at the target ablation location, the ablation can be performed. As described above, the path (target and/or actual) may be displayed on the graphic. In addition, when the EPDC is near the target ablation location, the EPDC may be activated at various activation locations and patient cardiograms collected. The IG system compares the patient cardiograms to a target cardiogram to identify patient cardiogram that matches the target cardiogram. The target cardiogram may have been identified by comparing patient cardiograms collected during an arrhythmia to library cardiograms to identify a source location (activation location) of the arrhythmia. When the patient cardiogram matches the target cardiogram, the activation location associated with the matching patient cardiogram may be used as the ablation location. More generally, the IG system may be used to track movement of various types of devices as the devices are moved through an organ and an EPDC is activated.

In some embodiments, the IG system may interface with a biomechanical simulation system to identify an initial target fixation location and to identify updated target fixation locations during an implantation procedure. Prior to the start of an implantation procedure, a biomechanical simulation system may initially perform simulations based on initial biomechanics of the patient's heart to identify an initial target fixation location. A target path can then be determined from the entry point into the vein to the initial target fixation position. During the implantation procedure, the electrophysiologist may determine that the biomechanics used in the simulation do not accurately represent the patient's actual biomechanics. In such a case, the biomechanical simulation system may perform simulations based on biomechanics derived from the patient's actual biomechanics (or assumed actual biomechanics) to identify an updated target fixation position. The IG system can then generate and display an updated target path from the current location of the EP DC to the updated target fixation position. A biomechanical simulation system is described in U.S. Patent Publication No. 2016/0262635 entitled "Compositions, Devices, and Methods for Diagnosing Heart Failure and for Patient-Specific Modeling to Predict Outcomes of Cardiac Resynchronization Therapy" and published on Sep. 15, 2016, which is hereby incorporated by reference.

In some embodiments, the IG system may interface with a control device that controls the movement of the EPDC to the fixation location. The control device may control movement of a catheter within the heart. The IG system may provide a next activation location to the control device. The control device controls movement of the EPDC to that next activation location. The control device then controls the EPDC to contact the endocardium and then activates the EPDC. The IG system receives a patient cardiogram and identifies the actual activation location (i.e., current location of EPDC), which may deviate from the target activation location. The control device may employ a mechanism to direct movement of the catheter (e.g., push, pull, twist, and bend) in a manner similar to how a cardiac electrophysiologist would control movement of the catheter.

In some embodiments, the IG system may employ a machine learning model to identify the activation location (current EPDC location) associated with a patient cardiogram. The machine learning model may be trained using the library cardiograms as feature vectors labeled with the associated activation locations as training data. The training of a machine learning model is described in U.S. Pat. No. 10,860,745. When the IG system receives a patient cardiogram, the IG system generates a feature vector that represents the patient cardiogram and applies the machine learning model to the feature vector to identify the activation location. The feature vectors may also represent source (heart) configuration data such as scar locations, cardiac orientation, electrical properties, and other attributes of the heart.

In some embodiments, the IG system may employ any of the technologies described in U.S. Pat. No. 10,860,745. For example, the IG system may employ a patient matching system to identify attributes of a patient's heart based on patient matching that is matching a patient source configuration (e.g., heart geometry) to model source configurations or clinical source configurations (of other patients). A patient cardiogram may be compared to library cardiograms to find a matching library cardiogram. The source configuration associated with the matching library cardiogram may represent the attributes (e.g., anatomical and electrophysiological properties) of the patient's heart. The identified attributes may be used as input to the biomechanical simulation system. The identified attributes and/or attributes identified in other ways (e.g., MRI measurements) may also be used to generate a patient-specific cardiogram library that includes library cardiograms associated with attributes similar to the attributes of the patient's heart. The patient matching system may provide a faster and more accurate identification of a matching cardiogram or a more accurate machine learning model (e.g., classifier) using the patient-specific cardiogram library. As another example, the IG system may calibrate the cardiogram library to the attributes of the patient by, for example, adjusting library cardiograms based on differences between attributes (e.g., cardiac orientation) associated with the library cardiograms and attributes of the patient.

In some embodiments, the IG system may employ a machine learning model to generate a target path and/or adjust a target path during a procedure (e.g., implantation or ablation). A machine learning model for generating a target path may be trained using training data that includes feature vectors representing features such as current location (e.g., an entry point or activation location), cardiac geometry, and scar locations along with an entry point and a target fixation location. The feature vectors may be labeled with a target path from the entry to the target fixation location. To determine a target path for a patient, a feature vector for the patient is generated and input to the machine learning model, which outputs a target path from the entry point to the target fixation location. To adjust a target path during a procedure, a feature vector is generated based on the current location and input to the machine learning model, which outputs a target path from the current location to the target fixation location.

In some embodiments, the IG system interfaces with a simulation system that employs a computational model of the electromagnetic source (e.g., an organ) to generate the library that may be used to train a machine learning model. A computational model models electromagnetic output of the electromagnetic source over time based on a source configuration of the electromagnetic source. The electromagnetic output may represent electrical potential, current, magnetic field, and so on. When the electromagnetic ("EM") source is a heart, the source configuration (or source attributes) may include any subset of the group consisting of information on geometry and muscle fibers of the heart, torso anatomy, normal and abnormal cardiac anatomy, normal and abnormal cardiac tissue, scar, fibrosis, inflammation, edema, accessory pathways, congenital heart disease, malignancy, sites of prior ablation, sites of prior surgery, sites of external radiation therapy, pacing leads, implantable cardioverter-defibrillator leads, cardiac resynchronization therapy leads, pacemaker pulse generator location, implantable cardioverter-defibrillator pulse generator location, subcutaneous defibrillator lead location, subcutaneous defibrillator pulse generator location, leadless pacemaker location, other implanted hardware (e.g., right or left ventricular assist devices), external defibrillation electrodes, surface ECG leads, surface mapping leads, a mapping vest, other normal and pathophysiologic feature distributions, and so on, and the EM output is a collection of the electric potentials at various heart locations over time. To generate the EM output, a simulation may be performed for simulation steps of a step size (e.g., 1 ms) to generate an EM mesh for that step. The EM mesh may be a finite-element mesh that stores the value of the electric potential at each heart location for that step. For example, the left ventricle may be defined as having approximately 70,000 heart locations with the EM mesh storing an electromagnetic value for each heart location. If so, a three-second simulation with a step size of 1 ms would generate 3,000 EM meshes that each include 70,000 values. The collection of the EM meshes is the EM output for the simulation. A computational model is described in C. T. Villongco, D. E. Krummen, P. Stark, J. H. Omens, & A. D. McCulloch, "Patient-specific modeling of ventricular activation pattern using surface ECG-derived vectorcardiogram in bundle branch block," Progress in Biophysics and Molecular Biology, Volume 115, Issues 2-3, August 2014, Pages 305-313, which is hereby incorporated by reference. In some embodiments, the simulation system may generate values for points between the vertices as the mesh, rather than just at the vertices. For example, the simulation system may calculate the values for such points using a Gaussian quadrature technique.

In some embodiments, the simulation system generates the training data by running many simulations, each based on a different source configuration, which is a set of different values for the configuration parameters of the computational model. For example, the configuration parameters for the heart may be cardiac geometry, rotor location, focal source location, ventricular orientation in the chest, ventricular myofiber orientation, cardiomyocyte intracellular potential electrogenesis and propagation, and so on. Each configuration parameter may have a set or range of possible values. For example, the rotor location may be 78 possible parameter sets corresponding to different locations within a ventricle. Since the system may run a simulation for each combination of possible values, the number of simulations may be in the millions.

In some embodiments, the simulation system uses EM outputs of the simulations to train a classifier for the generation of a classification based on EM data collected from a patient. The simulation system may generate derived EM data for each EM output of a simulation. The derived EM data correspond to EM data generated based on measurements that would be collected by an EM measuring devices that use, for example, 12 leads to generate an electrocardiogram (ECG) or a vectorcardiogram (VCG), a body surface vest, an intra-electromagnetic source device, and so on. The ECG and VCG are equivalent source representations of the EM output. The simulation system then generates a label (or labels) for each derived EM data to specify its corresponding classification. For example, the simulation system may generate a label that is the value of a configuration parameter (e.g., rotor location) used when generating the EM output from which the EM data was derived. The collection of the derived EM data, which correspond to feature vectors, and their labels compose the training data for training the classifier. The simulation system then trains the classifier. The classifier may be any of a variety or combination of classifiers including neural networks such as fully-connected, convolutional, recurrent, autoencoder, or restricted Boltzmann machine, a support vector machine, a Bayesian classifier, and so on. When the classifier is a deep neural network, the training results in a set of weights for the activation functions of the deep neural network. The classifier selected may be based on the type of disorder to be identified. For example, certain types of neural networks may be able to effectively train based on focal sources, but not rotor sources.

Figure 1:
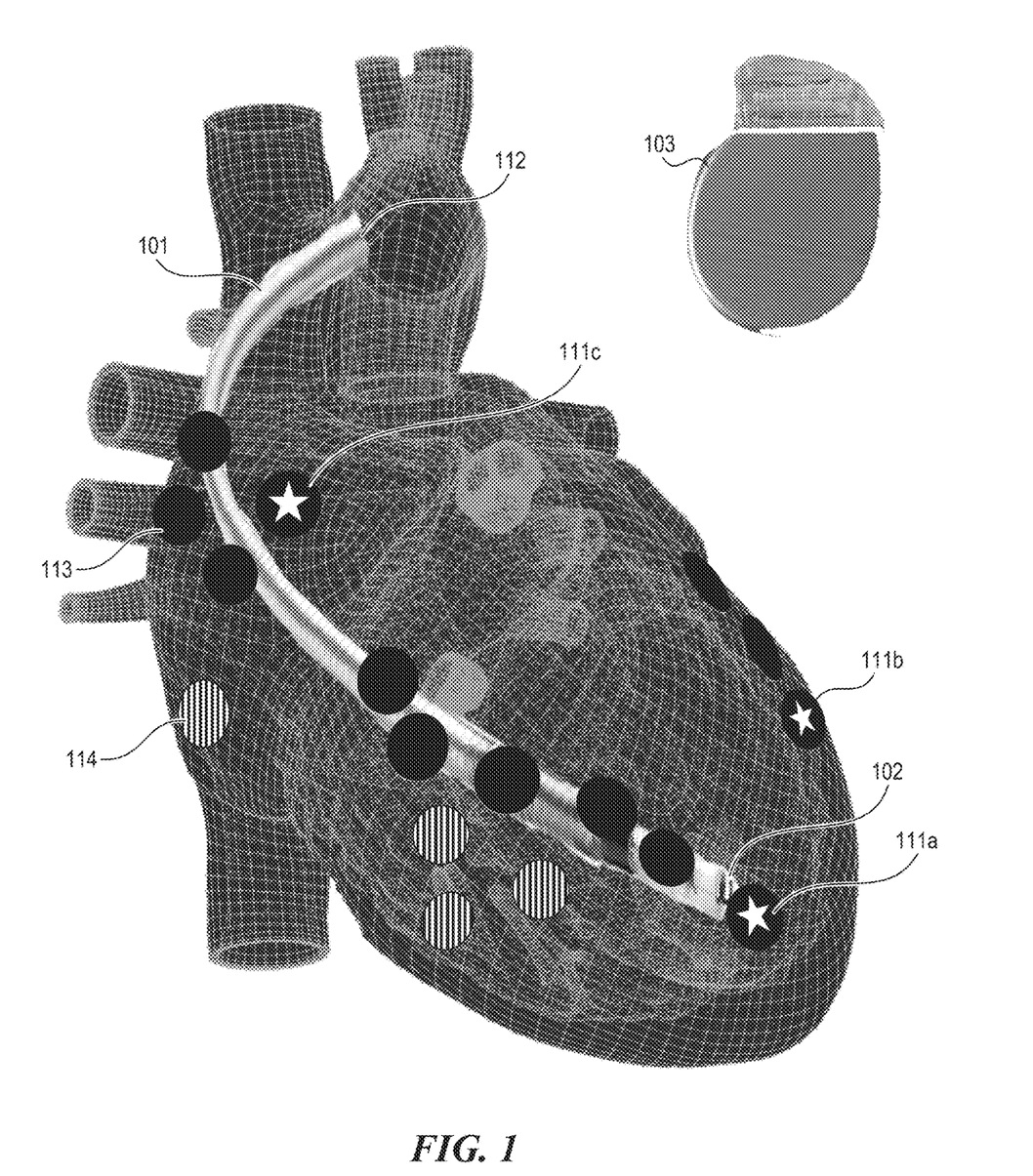
FIG. 1 illustrates a graphic of a heart showing a lead and an energy pulse generator component (EPDC) to be implanted.

FIG. 1 illustrates a graphic of a heart showing a lead and an EPDC to be implanted. A heart graphic 100 has superimposed on it a lead 101 and an EPDC 102. An EPGC 103 is illustrated adjacent to the heart graphic. Circles (with stars) 111a, 111b, and 111c represent target fixation locations for three EPDCs. EPDC 102 is illustrated positioned at fixation location 111a. Circles 113 (black) represent activation locations along the target path from entry point 112 to circle 111a. Circles 114 (striped) represent activation points that deviated from the target path. The circles indicating activation locations may be color coded to indicate amount of deviation from the target path.

Figure 2:
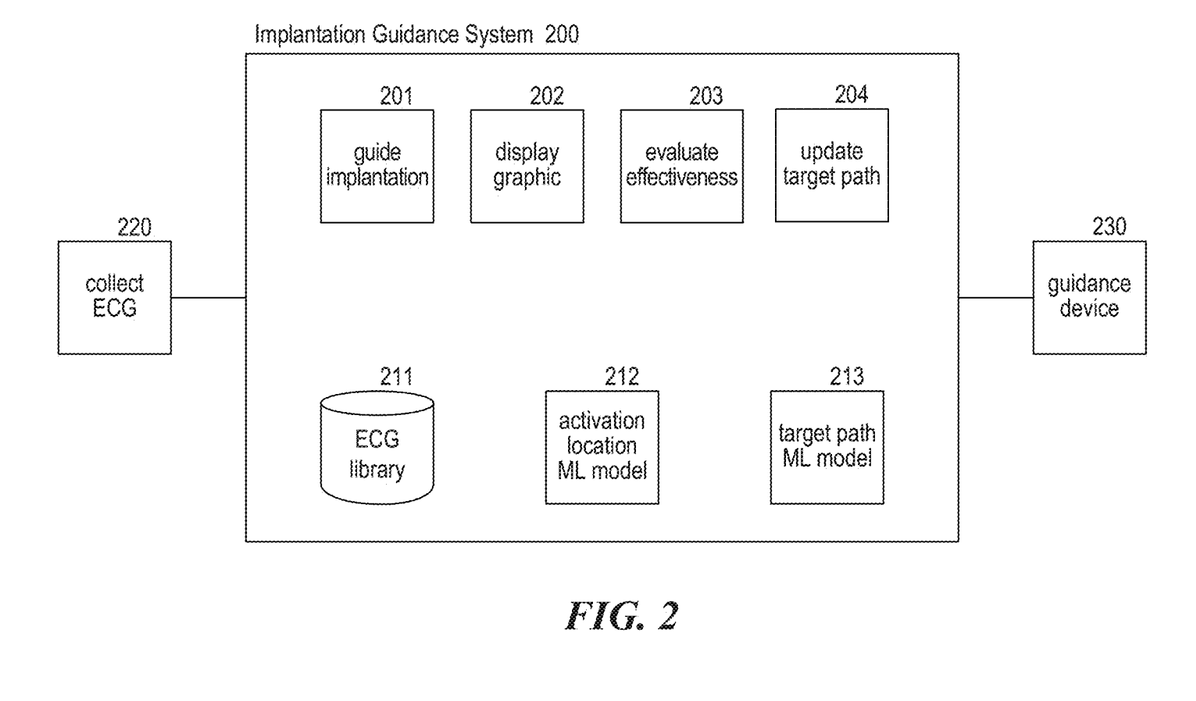
FIG. 2 is a block diagram that illustrates components of the implantation guidance system in some embodiments.

FIG. 2 is a block diagram that illustrates components of the implantation guidance system in some embodiments. The IG system 200 includes a guide implantation component 201, a display graphic component 202, an evaluate effectiveness component 203, and an update target path component 204. The guide implantation component inputs a fixation location and ECGs collected from a patient will pacing that an activation location during an implantation procedure. The guide implantation component identifies an activation location for each ECG and outputs an indication of the activation location to guide the implantation procedure. The display graphic component displays a graphic of a heart along with a target path and indications of activation locations and the target fixation location. The evaluate effectiveness component coordinates the assessing effectiveness of various candidate fixation locations that are near a target fixation location. The update target path component employs a biomechanical simulation system to update the target path during an implantation procedure based on updated attributes of the patient's heart. The IG system also includes an ECG library 211, and activation location machine learning model 212, and a target path machine learning model 213. The ECG library includes simulated ECGs and/or patient ECGs that are associated with activation locations resulting in the corresponding ECGs. The activation location machine learning model inputs a feature vector that includes an ECG and may include other heart configuration information of the patient and outputs corresponding activation location. The target path machine learning model inputs a current location and a fixation location and outputs a target path from the current location to the fixation location. The IG system inputs and ECG from a collective ECG component 220 and outputs activation locations to a guidance device 230.

The computing systems (e.g., network nodes or collections of network nodes) on which the IG system and the other described systems may be implemented may include a central processing unit, input devices, output devices (e.g., display devices and speakers), storage devices (e.g., memory and disk drives), network interfaces, graphics processing units, cellular radio link interfaces, global positioning system devices, and so on. The input devices may include keyboards, pointing devices, touch screens, gesture recognition devices (e.g., for air gestures), head and eye tracking devices, microphones for voice recognition, and so on. The computing systems may include high-performance computing systems, cloud-based servers, desktop computers, laptops, tablets, e-readers, personal digital assistants, smartphones, gaming devices, servers, and so on. For example, the simulations and training may be performed using a high-performance computing system, and the classifications may be performed by a tablet. The computing systems may access computer-readable media that include computer-readable storage media and data transmission media. The computer-readable storage media are tangible storage means that do not include a transitory, propagating signal. Examples of computer-readable storage media include memory such as primary memory, cache memory, and secondary memory (e.g., DVD) and other storage. The computer-readable storage media may have recorded on them or may be encoded with computer-executable instructions or logic that implements the IG system and the other described systems. The data transmission media are used for transmitting data via transitory, propagating signals or carrier waves (e.g., electromagnetism) via a wired or wireless connection. The computing systems may include a secure cryptoprocessor as part of a central processing unit for generating and securely storing keys and for encrypting and decrypting data using the keys to preserve privacy of patient information such as required by Health Insurance Portability and Accountability Act (HIPAA).

The IG system and the other described systems may be described in the general context of computer-executable instructions, such as program modules and components, executed by one or more computers, processors, or other devices. Generally, program modules or components include routines, programs, objects, data structures, and so on that perform tasks or implement data types of the IG system and the other described systems. Typically, the functionality of the program modules may be combined or distributed as desired in various examples. Aspects of the IG system and the other described systems may be implemented in hardware using, for example, an application-specific integrated circuit ("ASIC") or field programmable gate array ("FPGA").

The machine learning models employ by the IG system may be any of a variety or combination of classifiers including neural networks such as fully-connected, convolutional, recurrent, autoencoder, or restricted Boltzmann machine; a support vector machine; a Bayesian classifier; and so on. When the machine learning model is a deep neural network, the training results in a set of weights for the activation functions of the deep neural network. A neural network model has three major components: architecture, cost function, and search algorithm. The architecture defines the functional form relating the inputs to the outputs (in terms of network topology, unit connectivity, and activation functions). The search in weight space for a set of weights that minimizes the objective function is the training process. In one embodiment, the IG system may use a radial basis function ("RBF") network and a standard gradient descent as the search technique.

Figure 3:
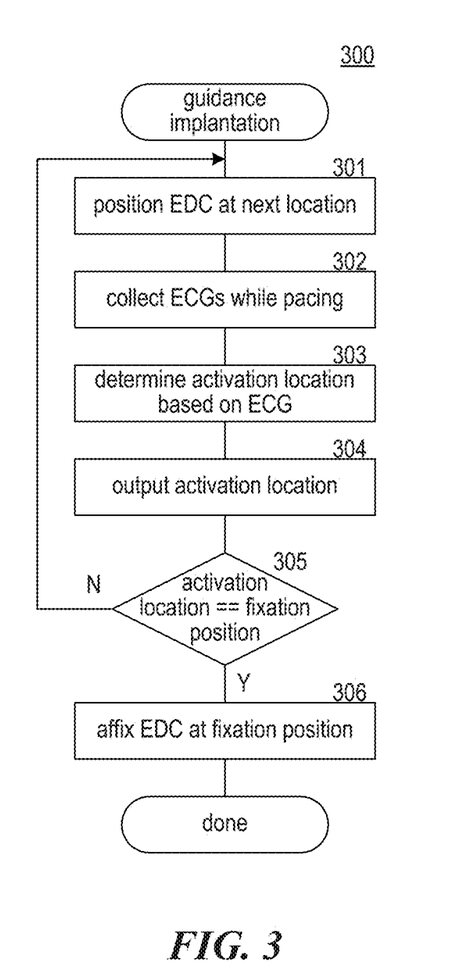
FIG. 3 is a diagram that illustrates the processing of the guide implantation component of the IG system in some embodiments.

FIG. 3 is a diagram that illustrates the processing of the guide implantation component of the IG system in some embodiments. The guide implementation component 300 repeatedly receives ECGs and outputs an indication of the current location of the EPDC. In block 301, the component receives an indication that the EPDC has been positioned at an activation location. In block 302, the component collects patient ECGs during pacing at the activation location. In block 303, the component determines the activation location based on the patient ECG, for example, by identifying a matching library ECG or applying machine learning model that inputs the patient ECG. In block 304, the component outputs an indication of the activation location. In decision block 305, if the activation location corresponds to the fixation location, then the component continues at block 306, else the component loops to block 301 to process the next positioning of the EPDC. In block 306, the component directs the affixing of the EPDC at the fixation location and then completes.

Figure 4:
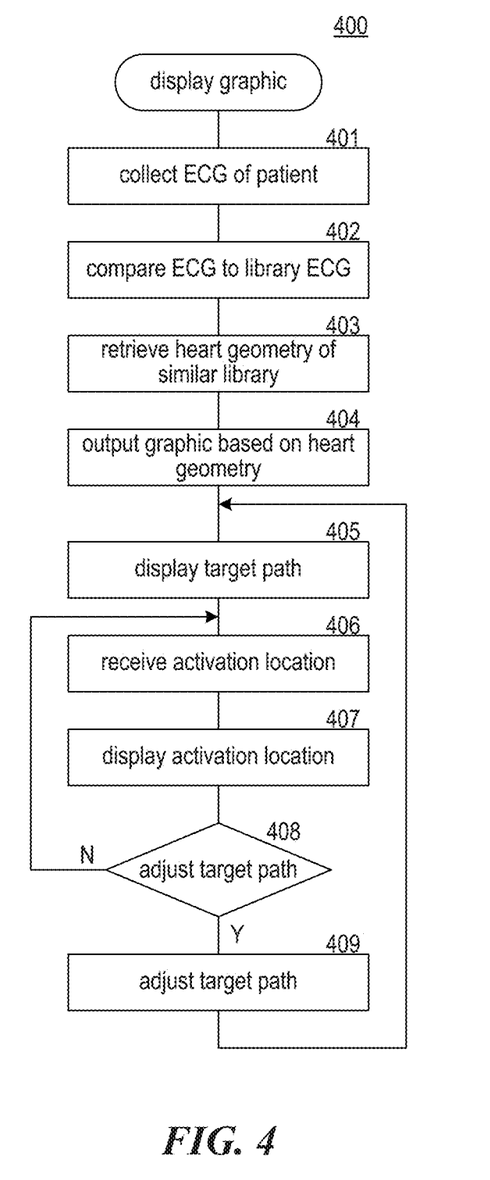
FIG. 4 is a flow diagram that illustrates the processing of the display graphic component of the IG system in some embodiments.

FIG. 4 is a flow diagram that illustrates the processing of the display graphic component of the IG system in some embodiments. The display graphic 400 receives activation locations and displays an indication of the current locations of the EPDC on a graphic of a heart. In block 401, the component receives an ECG collected from the patient. In block 402, the component compares the patient ECG to library ECGs to identify a matching library ECG. In block 403, the component retrieves the heart geometry associated with the matching library ECG. In block 404, the component outputs a graphic based on the heart geometry with the target fixation location highlighted. In blocks 405-409, the component loops processing each activation location. In block 405, the component displays a target path. In block 406, the component receives an indication of the current activation location. In a block 407, the component displays an indication of the activation location. The displayed indication may be color coded to indicate whether the current activation location is along the target path or deviates from the target path. The shading of the color may indicate the amount of deviation from the target path. In decision block 408, if the target path needs to be adjusted based on a deviation, then the component continues at block 409, else the component loops to block 406 to receive the next activation location. In block 409, the component adjusts the target path and loops to block 4052 display the adjusted target path.

Figure 5:
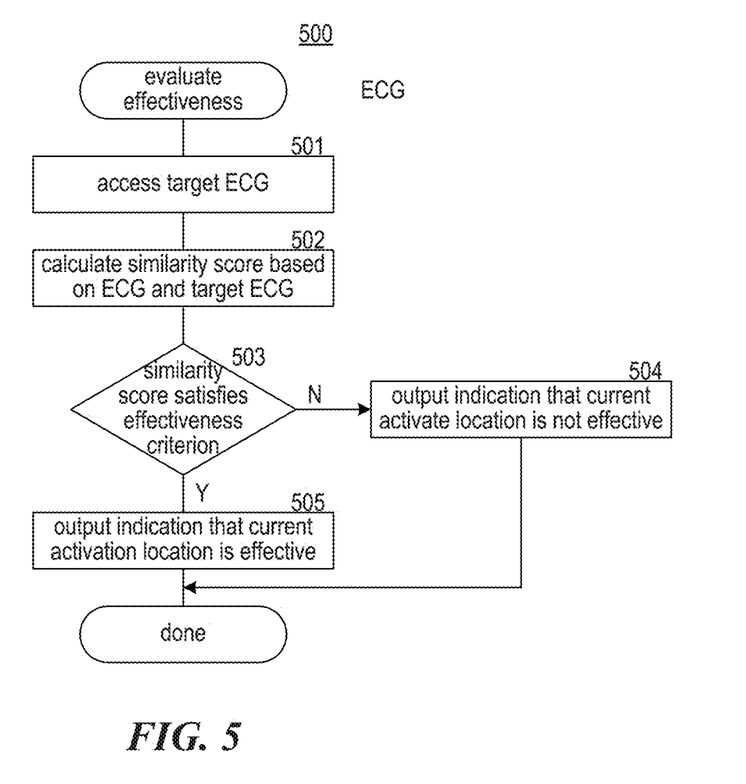
FIG. 5 is a flow diagram that illustrates the processing of an evaluate effectiveness component of the IG system in some embodiments.

FIG. 5 is a flow diagram that illustrates the processing of an evaluate effectiveness component of the IG system in some embodiments. The evaluate effectiveness component 500 is provided a patient ECG and outputs an indication of whether the activation location associated with the patient ECG would be effective at treating the arrhythmia. In block 501, the component accesses a target ECG. In block 502, the component calculates a similarity score indicating similarity between the patient ECG and the target ECG. For example, the similarity score may be based on vector distance between VCGs derived from the ECGs. Other techniques to assessing similarity are described in U.S. Pat. No. 10,860, 745. In decision block 503, if the similarity score satisfies an effectiveness criterion, then the component continues at block 505, else the component continues at block 504. The effectiveness criterion may be based on a maximum vector distance threshold, on comparison to the vector distances associated with candidate fixation location, and so on. In block 504, the component outputs an indication that the current activation location is not effective and completes. In block 505, the competent output indication that the current activation location is effective and then completes.

Figure 6:
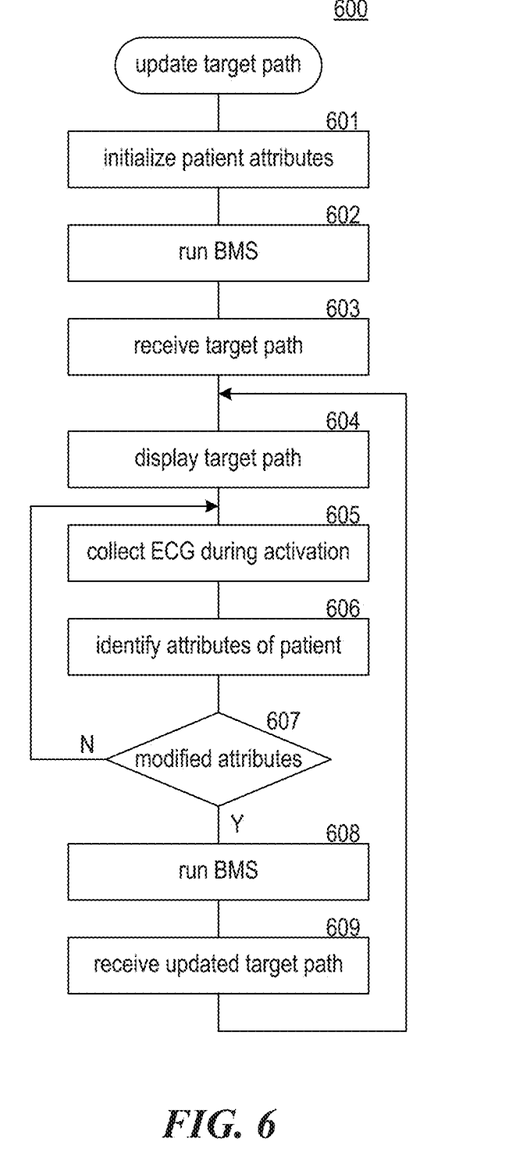
FIG. 6 is a flow diagram that illustrates the processing of the update target path component of the IG system in some embodiments.

FIG. 6 is a flow diagram that illustrates the processing of the update target path component of the IG system in some embodiments. The update target path component 600 is invoked during an implantation procedure to update the target path based on updated information on attributes of the patient's heart. In block 601, the component initializes the patient's attributes. In block 602, the component runs a biomechanical simulation to generate a target path based on the patient's attributes. In block 603, the component receives the target path. In block 604, the component displays the target path. In block 605, the component collects a cardiogram from the patient during pacing at an activation location. In block 606, the component identifies attributes of the patient, for example, based on comparison of the cardiogram to library cardiograms and/or based on input from the electrophysiologist. In decision block 607, if the attributes have been modified, then the component continues at block 608, else the component continues at block 605 to collect the next cardiograms. In block 608, the component runs a biomechanical simulation based on the modified attributes to generate an updated target path. In block 609, the component receives the updated target path and loops to block 604 to display the updated target path.

The following paragraphs describe various embodiments of aspects of the IG system and other system. An implementation of the systems may employ any combination of the embodiments. The processing described below may be performed by a computing system with a processor that executes computer-executable instructions stored on a computer-readable storage medium that implements the system.

In some embodiments, A method performed by one or more computing systems is provided for guiding implantation of an energy delivery component of implantable device at a fixation location within a heart of a patient. The implantable device having an energy source component that provides energy to the energy delivery component. During implantation of the energy delivery component, the method repeatedly receives a patient cardiogram collected during pacing of the energy delivery component while the energy delivery component is positioned at a current location within the heart; determines from the patient cardiogram the current location of the energy delivery component; and outputs an indication of the current location to guide affixing of the energy delivery component at the fixation location. In some embodiments, the outputting includes displaying a representation of a heart with an indication of the current location of the energy delivery component. In some embodiments, the displayed representation further includes an indication of a target path from entry into the heart to the fixation location. In some embodiments, 4 the display representation further includes an indication of deviation of a current location from the target path. In some embodiments, the determining includes applying a machine learning model to the patient cardiogram to identify the current location. The machine learning model may be trained with training data that includes training cardiograms labeled with activation locations. In some embodiments, the training cardiograms may be derived from simulations of electrical activity of a heart given an activation location, collected from patients, or both. In some embodiments, the training data is based on similarity between characteristics of the patient's heart and characteristics of a heart used in generating the training data. In some embodiments, the method further analyzes a patient cardiogram to evaluate effectiveness of the current location as a fixation location for the energy delivery component. In some embodiments, the effectiveness is based on similarity of the patient cardiogram to a target cardiogram. In some embodiments, the determining includes accessing a library of mappings of library cardiograms to activation locations to identify a library cardiogram that is similar to the patient cardiogram wherein the current location is determined based on an activation location associated with a library cardiogram that is similar to the patient cardiogram. In some embodiments, the cardigram library is a patient-specific library. In some embodiments, the method further comprising, when the current location deviates from a target path from entry into the heart to the fixation location, generating an updated target path from the current location to the fixation location. In some embodiments, the generating of the updated target path includes applying a machine learning model trained using target paths and current locations labeled with updated target paths. In some embodiments, the outputting indicates when the current location is the target location. In some embodiments, the outputting provides an indication of a next location for pacing. In some embodiments, the method further comprises identifying from a cardiogram library a library cardiogram that is similar to the patient cardiogram and wherein the outputting includes displaying a representation heart-related anatomical geometry associated with the similar library cardiogram with an indication of the current location of the energy delivery component. In some embodiments, the indication is output to a device that controls guiding of the energy delivery component. In some embodiments, the energy delivery component is guided through the atria and then into a ventricle. In some embodiments, the energy delivery component is guided into the atrium, through the ostium of the coronary sinus, into the body of the coronary sinus, and out a branch of the coronary sinus.

In some embodiments, a method performed by one or more computing systems is provided for evaluating effectiveness of possible fixation locations during implantation of an energy delivery component of a cardiac device. The cardiac device has an energy source component that provides energy to the energy delivery component. The method, during implantation of the energy delivery component repeatedly, receives a patient cardiogram collected during pacing of the energy delivery component while the energy delivery component is positioned at a candidate fixation location; evaluates effectiveness of the candidate fixation location based on the patient cardiogram; and outputs an indication of the effectiveness of the candidate fixation location. In some embodiments, the outputting includes displaying a representation of a heart with an indication of the candidate fixation location of the energy delivery component. In some embodiments, the evaluating of the effectiveness is based on comparison of the patient cardiogram to a target cardiogram. In some embodiments, the evaluating includes applying a machine learning model to the patient cardiogram to generate an indication of effectiveness of the candidate fixation location, the machine learning model being trained with training data that includes training cardiograms labeled with indications of effectiveness. In some embodiments, the training cardiograms are derived from simulations of electrical activity of a heart given an activation location. In some embodiments, the training cardiograms are collected from patients. In some embodiments, the training data is based on similarity between characteristics of the patient's heart and characteristics of a heart used in generating the training data. In some embodiments, the method further comprises determining from the patient cardiogram a current location of the energy delivery component. In some embodiments, the determining includes accessing a library of mappings of library cardiograms to activation locations to identify a library cardiogram that is similar to the patient cardiogram wherein the current location is determined based on an activation location associated with a library cardiogram that is similar to the patient cardiogram. In some embodiments, the method further comprises identifying from of a cardiogram library a library cardiogram that is similar to the patient cardiogram and wherein the outputting includes displaying a representation heart-related anatomical geometry associated with the similar library cardiogram with an indication of the candidate fixation. In some embodiments, the evaluating includes determining similarity between the patient cardiogram and a target cardiogram.

In some embodiments, a method performed by one or more computing systems is provided for tracking location of a catheter within a heart. The catheter has an energy delivery component that receives energy from an energy source component. The method while the catheter is within a heart repeatedly receives a patient cardiogram collected during pacing of the energy delivery component while the energy delivery component is positioned at a current location within the heart; determines from the patient cardiogram the current location of the energy delivery component; and outputs an indication of the current location to track the catheter while within the heart.

In some embodiments, one or more computing systems are provided for guiding implantation of an energy delivery component at a fixation location within an organ of a patient. The energy delivery component is for receiving energy from an energy source component. The one or more computing system comprises one or more computer-readable storage mediums for storing computer-executable instructions for controlling the one or more computing systems and one or more processors for executing the computer-executable instructions stored in the one or more computer-readable storage mediums. The instructions control the one or more computing systems to repeatedly, during implantation of the energy delivery component receive a patient electrogram collected after delivery of energy via the energy delivery component while the energy delivery component is positioned at a current location within the organ; determine from the patient cardiogram the current location of the energy delivery component; and output an indication of the current location to guide affixing of the energy delivery component at the fixation location.

Although the subject matter has been described in language specific to structural features and/or acts, it is to be understood that the subject matter defined in the appended claims is not necessarily limited to the specific features or acts described above. Rather, the specific features and acts described above are disclosed as example forms of implementing the claims. Accordingly, the invention is not limited except as by the appended claims.

The invention claimed is:

1. A method performed by one or more computing systems for guiding implantation of an energy delivery component of a cardiac device at a fixation location within a heart of a patient, the cardiac device having an energy source component that provides energy to the energy delivery component, the method comprising:
 prior to starting implantation of the energy delivery component,
  accessing an indication of the fixation location;
  generating a target path to guide movement of the energy delivery component from entry into the heart to the fixation location;
  displaying a representation of a heart; and
  displaying a representation of the target path superimposed on the representation of the heart; and
 during implantation of the energy delivery component repeatedly performing the following until the energy delivery component is determined to be at the fixation location:
  receiving a patient cardiogram collected during pacing of the energy delivery component while the energy delivery component is positioned at a current location within the heart;
  determining the current location of the energy delivery component by applying a first machine learning model to the patient cardiogram to identify the current location of the energy delivery component, the first machine learning model being trained with training data that includes training cardiograms labeled with activation locations;
  displaying on the representation of the heart an indication of the current location of the energy delivery component relative to the displayed target path; and
  determining whether the energy delivery component is at the fixation location.

2. A method performed by one or more computing systems for guiding implantation of an energy delivery component of a cardiac device at a fixation location within a heart of a patient, the cardiac device having an energy source component that provides energy to the energy delivery component, the method comprising:
 accessing training data that includes training cardiograms labeled with pacing locations;
 training a first machine learning model using the training data; and
 during implantation of the energy delivery component repeatedly:
  receiving a patient cardiogram collected during pacing of the energy delivery component while the energy delivery component is positioned at a current location within the heart;
  determining from the patient cardiogram the current location of the energy delivery component without using imaging data collected from the patient; and
  outputting an indication of the current location to guide affixing of the energy delivery component at the fixation location wherein the determining includes applying the first learning model to the patient cardiogram to identify the current location of the energy delivery component.

3. A method performed by one or more computing systems for guiding implantation of an energy delivery component of a cardiac device at a fixation location within a heart of a patient, the cardiac device having an energy source component that provides energy to the energy delivery component, the method comprising:
 accessing training data that includes training target paths and pacing locations labeled with updated target paths;
 training a machine learning model using the training data;
 prior to starting implantation of the energy delivery component, generating a current target path within the heart to the fixation location; and
 during implantation of the energy delivery component repeatedly:
  displaying on a representation of a heart the current target path;
  receiving a patient cardiogram collected during pacing of the energy delivery component while the energy delivery component is positioned at a current location within the heart;
  determining from the patient cardiogram the current location of the energy delivery component;
  outputting an indication of the current location to guide affixing of the energy delivery component at the fixation location;
  determining whether the current location deviates from the current target path from entry into the heart to the fixation location; and
  when the current location deviates from the current target path from entry into the heart to the fixation location,
   applying the machine learning model to the current target path and the current location to generate an updated target path from the current location to the fixation location; and
   setting the current target path to the updated target path.

4. The method of claim 1 further comprising when the current location deviates from the target path, applying a second machine learning model to the target path and the current location to generate an updated target path, the second machine learning model trained using training data that includes training target paths and locations labeled with updated target paths.

5. The method of claim 2 further comprising prior to starting implantation of the energy delivery component, generating a target path within the heart to the fixation location and displaying the target path; and during implantation of the energy delivery component, determining whether the current location deviates from the target path, and when the current location deviates from the target path, applying a second machine learning model to the target path and the current location to generate an updated target path and displaying an indication of the updated target path, the second machine learning model trained using training data that includes training target paths and locations labeled with updated target paths.

6. One or more computing systems for guiding implantation of an energy delivery component of a cardiac device at a fixation location within a heart of a patient, the cardiac device having an energy source component that provides energy to the energy delivery component, the one or more computing systems comprising:

one or more computer-readable storage mediums storing
a library of library cardiograms and pacing locations,
each pacing location being associated with a library
cardiogram that would be collected when a heart is
paced at that pacing location, the library cardiograms
not being collected from the patient; and computer-executable instructions for controlling the
one or more computing systems to during implantation of the energy delivery component to repeatedly
perform the following until the energy delivery component is determined to be at the fixation location:

receive a patient cardiogram collected during pacing
of the energy delivery component while the
energy delivery component is positioned at a
current location within the heart;

compare the patient cardiogram to library cardiograms to identify a library cardiogram that is
similar to the patient cardiogram;

determine that the current location of the energy
delivery component is the pacing location associated with the identified library cardiogram;

output an indication of the current location to guide
affixing of the energy delivery component at the
fixation location; and determine whether the energy delivery component is
at the fixation location; and one or more processors for executing the computer-executable instructions stored in the one or more computer-readable storage mediums.

* * * * *

UNITED STATES PATENT AND TRADEMARK OFFICE
CERTIFICATE OF CORRECTION

PATENT NO. : 11,338,131 B1
APPLICATION NO. : 17/308400
DATED : May 24, 2022
INVENTOR(S) : Robert Joseph Krummen It is certified that error appears in the above-identified patent and that said Letters Patent is hereby corrected as shown below:

On the Title Page

On the page 2, in Column 1, under "U.S. Patent Documents", Line 39, delete "Gavit-Houdant" and insert -- Gavit-Houdant et al. --.

On the page 2, in Column 2, under "Other Publications", Line 10, delete "Intellegence" and insert -- Intelligence --.

On the page 2, in Column 2, under "Other Publications", Line 13, delete "arrhythima" and insert -- arrhythmia --.

On the page 3, in Column 1, under "Other Publications", Line 2, delete "20212;" and insert -- 2012; --.

On the page 3, in Column 1, under "Other Publications", Line 38, delete ""Recontruction" and insert -- "Reconstruction --.

On the page 3, in Column 1, under "Other Publications", Line 55, delete "Continues" and insert -- Continuous --.

On the page 3, in Column 2, under "Other Publications", Line 20, delete "1-17)." and insert -- 1-17. --.

On the page 3, in Column 2, under "Other Publications", Line 22, delete "PhysioloQy" and insert -- Physiology --.

On the page 3, in Column 2, under "Other Publications", Line 54, delete "Electrocardiagram"," and insert -- Electrocardiogram", --.

Signed and Sealed this
Fifteenth Day of October, 2024

Katherine Kelly Vidal
*Director of the United States Patent and Trademark Office*

CERTIFICATE OF CORRECTION (continued)
U.S. Pat. No. 11,338,131 B1

In the Specification

In Column 2, Line 24, delete "(EPDC)" and insert -- (EPGC) --.

In Column 10, Line 53, delete "A" and insert -- a --.

In Column 11, Line 29, delete "cardigram" and insert -- cardiogram --.

In the Claims

In Column 14, Line 1, in Claim 2, delete "first" and insert -- first machine --.